(12) United States Patent
Peters et al.

(10) Patent No.: US 8,901,344 B2
(45) Date of Patent: Dec. 2, 2014

(54) PRODUCTION OF CARBOXYLIC ACID ESTERS BY STRIPPING WITH ALCOHOL VAPOR

(75) Inventors: Jarren Peters, Mannheim (DE); Walter Disteldorf, Wachenheim (DE); Katrin Friese, Mannheim (DE); Thomas Schäfer, Mannheim (DE); Oliver Bey, Niederkirchen (DE)

(73) Assignee: BASF SE (DE)

( * ) Notice: Subject to any disclaimer, the term of this patent is extended or adjusted under 35 U.S.C. 154(b) by 325 days.

(21) Appl. No.: 13/140,274

(22) PCT Filed: Dec. 15, 2009

(86) PCT No.: PCT/EP2009/067179
§ 371 (c)(1),
(2), (4) Date: Jun. 16, 2011

(87) PCT Pub. No.: WO2010/076194
PCT Pub. Date: Jul. 8, 2010

(65) Prior Publication Data
US 2011/0301377 A1  Dec. 8, 2011

(30) Foreign Application Priority Data
Dec. 16, 2008 (EP) .................... 08171795

(51) Int. Cl.
C07C 67/08 (2006.01)
B01D 19/00 (2006.01)
B01D 3/38 (2006.01)
B01D 3/36 (2006.01)

(52) U.S. Cl.
CPC ............ *B01D 19/0015* (2013.01); *C07C 67/08* (2013.01); *B01D 3/38* (2013.01); *B01D 3/36* (2013.01)
USPC ............................................. 560/99; 560/98

(58) Field of Classification Search
USPC ..................................................... 560/99, 98
See application file for complete search history.

(56) References Cited

U.S. PATENT DOCUMENTS

| | | | |
|---|---|---|---|
| 5,008,046 A | 4/1991 | Bremus et al. | |
| 5,349,075 A * | 9/1994 | van den Berg et al. | 554/170 |
| 5,849,972 A | 12/1998 | Vicari et al. | |
| 5,976,324 A | 11/1999 | Groschl et al. | |
| 6,271,410 B1 * | 8/2001 | John et al. | 558/443 |
| 6,916,950 B2 * | 7/2005 | Gubisch et al. | 560/204 |
| 6,963,014 B1 | 11/2005 | Zeller et al. | |
| 7,091,367 B2 * | 8/2006 | Moritz et al. | 554/170 |
| 2002/0028963 A1 | 3/2002 | Gubisch et al. | |
| 2004/0106813 A1 | 6/2004 | Moritz et al. | |
| 2010/0270934 A1 | 10/2010 | Breuer et al. | |
| 2010/0312023 A1 | 12/2010 | Henkelmann et al. | |
| 2010/0312024 A1 | 12/2010 | Henkelmann et al. | |
| 2011/0028579 A1 | 2/2011 | Zoellinger et al. | |
| 2011/0028761 A1 | 2/2011 | Bock et al. | |

FOREIGN PATENT DOCUMENTS

| | | |
|---|---|---|
| DE | 2503195 A1 | 7/1976 |
| EP | 0334154 A2 | 9/1989 |
| EP | 0434390 A1 | 6/1991 |
| EP | 680463 A1 | 11/1995 |
| EP | 835860 A1 | 4/1998 |
| EP | 1186593 A2 | 3/2002 |
| WO | WO-92/13818 A1 | 8/1992 |
| WO | WO-94/17028 A1 | 8/1994 |
| WO | WO-95/14647 A1 | 6/1995 |
| WO | WO-01/36356 A2 | 5/2001 |

OTHER PUBLICATIONS

H. Suter, Chemie-Ing.-Technik 41 (1969), No. 17, pp. 971-974.

* cited by examiner

*Primary Examiner* — Sudhakar Katakam
*Assistant Examiner* — Pancham Bakshi
(74) *Attorney, Agent, or Firm* — Drinker Biddle & Reath LLP

(57) ABSTRACT

The invention relates to a method for producing carboxylic acid esters by reacting a reaction mixture, comprising a carboxylic acid and/or a carboxylic acid anhydride, and an alcohol in a reaction system having one or more reactors, wherein reaction water is distilled off as an alcohol/water azeotrope with the exhaust vapor. In addition, the reaction mixture is treated with superheated alcohol vapor. The method allows the production of esters having a low acid number.

9 Claims, 1 Drawing Sheet

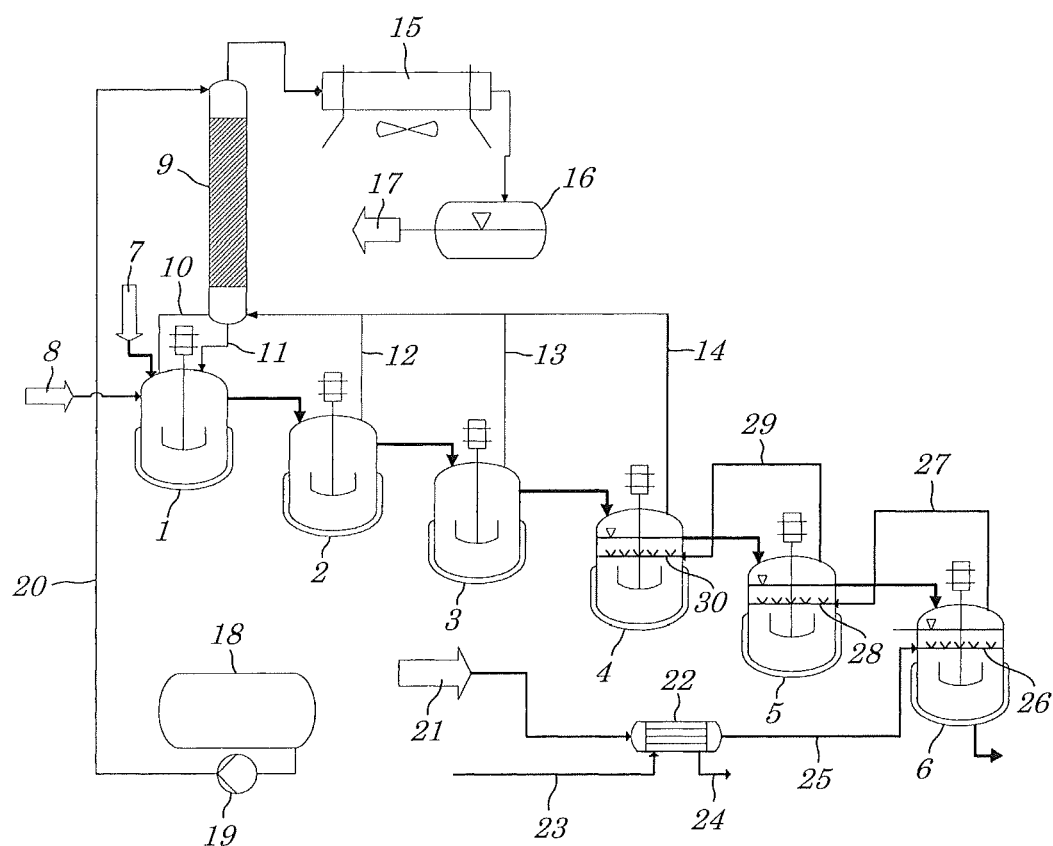

PRODUCTION OF CARBOXYLIC ACID ESTERS BY STRIPPING WITH ALCOHOL VAPOR

CROSS-REFERENCE TO RELATED APPLICATIONS

This application is a national stage application (under 35 U.S.C. §371) of PCT/EP2009/067179, filed Dec. 15, 2009, which claims benefit of European application 08171795.1, filed Dec. 16, 2008.

BACKGROUND OF THE INVENTION

The present invention relates to a process for preparing carboxylic esters by reaction of a reaction mixture comprising a carboxylic acid and/or a carboxylic anhydride and an alcohol.

Esters of phthalic acid, adipic acid, sebacic acid or maleic acid are widely employed in surface coating resins, as constituents of paints and in particular as plasticizers for plastics.

It is known that carboxylic esters can be prepared by reacting carboxylic acids with alcohols. This reaction can be carried out autocatalytically or catalytically, for example in the presence of Brönsted or Lewis acids as catalysts. Regardless of the type of catalysis, there is always a temperature-dependent equilibrium between the starting materials (carboxylic acid and alcohol) and the products (esters and water).

The reaction of internal carboxylic anhydrides with alcohols proceeds in two steps: the alcoholysis of the anhydride to form the monoester generally proceeds rapidly and to completion. The further conversion of the monoester into the diester with formation of water of reaction is reversible and proceeds slowly. This second step is the rate-determining step of the reaction.

To shift the equilibrium in the direction of the ester (or the full ester in the case of polybasic acids), it is usual to use an entrainer by means of which the water of reaction is removed from the mixture. If one of the starting materials (alcohol or carboxylic acid) has a boiling point lower than that of the ester formed and forms a miscibility gap with water, a starting material can be used as entrainer and be recirculated to the mixture after water has been separated off. In the esterification of higher aliphatic carboxylic acids, aromatic carboxylic acids or dibasic or polybasic carboxylic acids, the alcohol used is generally the entrainer. If the alcohol used serves as entrainer, it is usual to condense at least part of the vapor from the reactor, separate the condensate into an aqueous phase and an organic phase comprising essentially the alcohol used for the esterification and recirculate at least part of the organic phase to the reactor.

EP-A 1 186 593 describes a process for preparing carboxylic esters by reacting dicarboxylic or polycarboxylic acids or anhydrides thereof with alcohols, with the water of reaction being removed by azeotropic distillation with the alcohol. The amount of liquid removed from the reaction by the azeotropic distillation is replaced either completely or partly by the alcohol.

In Chemie-Ing.-Technik 41 (1969), No. 17, pp. 971-974, H. Suter describes the continuous preparation of phthalic esters in a cascade of stirred vessels.

The prior art comprises various proposals for improving the removal of the water of reaction.

Thus, EP 680 463 B1 describes a process for esterifying acids or acid anhydrides with a monoalcohol or a polyhydroxy compound, in which a reaction mixture is heated to boiling and water is removed as vapor and the reaction mixture is mixed continuously so that at least 2.5 volumes of reaction mixture are circulated internally per minute. The mixing under the stated conditions is said to increase the degree of conversion.

EP-A 835 860 relates to a process for separating off water from reaction mixtures for the esterification of acids or acid anhydrides with alcohols at the boiling point of the reaction mixture, in which the lowest-boiling starting material is firstly used in a substoichiometric amount, the resulting vapor mixture composed of predominantly water and the lowest-boiling component is dewatered over a membrane, the dewatered vapor mixture is recirculated to the reaction mixture and further amounts of the lowest-boiling starting material are added to the reaction mixture during the course of the reaction.

BRIEF SUMMARY OF THE INVENTION

It is an object of the invention to provide an alternative process for improving the removal of the water of reaction. A particular object of the invention is to provide a process for preparing esters having a low acid number.

The object is achieved by a process for preparing carboxylic esters by reaction of a reaction mixture comprising a carboxylic acid and/or a carboxylic anhydride and an alcohol in a reaction system comprising one or more reactors, with water of reaction being distilled off as alcohol-water azeotrope with the vapor, wherein the reaction mixture is treated with superheated alcohol vapor.

BRIEF DESCRIPTION OF THE DRAWING

FIG. 1 shows a plant suitable for carrying out the process of the invention.

DETAILED DESCRIPTION OF THE INVENTION

Superheated alcohol vapor has a temperature above the thermodynamically defined dew point at operating pressure. As alcohol vapor, use is made of the gaseous form of the alcohol which is the alcohol component of the reaction mixture. The temperature of the alcohol vapor is preferably at least 20° C. higher than the dew point.

The reaction mixture is advantageously treated with the alcohol vapor in such a way that a large exchange area between the liquid reaction mixture and the alcohol vapor is created, preferably under turbulent conditions. The treatment with alcohol vapor during the reaction has a stripping effect and completes the removal of the water of reaction. The alcohol vapor also introduces energy into the reaction system; the energy input via the reactor wall can be reduced. This enables overheating of the reaction mixture in the vicinity of the reactor wall and the formation of by-products to be decreased.

Apparatuses suitable for the treatment are, for example, all customary apparatuses for the stripping of liquids by means of gases.

In preferred embodiments, the alcohol vapor is introduced into the boiling reaction mixture below the surface of the liquid, so that it bubbles through the reaction mixture. The pressure of the alcohol vapor has to be sufficiently high to overcome the hydrostatic pressure of the reaction mixture above the point of introduction of the alcohol vapor. For example, the alcohol vapor can be introduced at from 20 to 50 cm below the surface of the liquid reaction mixture.

The alcohol vapor can be fed in via any suitable devices. Suitable devices are, for example, sparging lances which can be fixed in position or preferably nozzles. The nozzles can be provided at or in the vicinity of the bottom of the reactor. The nozzles can for this purpose be configured as openings from a hollow chamber surrounding the reactor. However, preference is given to using immersed nozzles with suitable feed lines. A plurality of nozzles can, for example, be arranged in the form of a ring. The nozzles can point upward or downward. The nozzles preferably point obliquely downward.

The reaction mixture is preferably mixed in order to effect exchange of reaction mixture in the reactor region below the introduction of alcohol vapor with reaction mixture in the reactor region above the introduction of alcohol vapor. Mixing can be achieved by, for example, stirrers or a circulation pump.

The alcohol vapor is preferably produced by vaporization of liquid, water-free alcohol. The alcohol vapor can be produced in any vapor generator, e.g. a boiler, plate vaporizer, tube vaporizer or shell-and-tube vaporizer. Plate and shell-and-tube vaporizers and combinations thereof are generally preferred.

The amount of alcohol vapor introduced is not subject to any particular restrictions and when the process is carried out continuously is, for example, from 0.01 to 0.5 kg/h, in particular from 0.05 to 0.2 kg/h, per kg/h of reaction mixture.

For the purposes of the present invention, a "reaction system" is a reactor or an assembly of a plurality of reactors. In the case of a plurality of reactors, these are preferably connected in series. The process of the invention can be carried out batchwise or continuously, but is preferably carried out continuously.

The reactors can be any reactors which are suitable for carrying out chemical reactions in the liquid phase.

Suitable reactors are reactors which are not backmixed, e.g. tube reactors or residence vessels provided with internals, but preferably backmixed reactors such as stirred vessels, loop reactors, jet loop reactors or jet nozzle reactors. However, combinations of successive backmixed reactors and reactors which are not backmixed can also be used.

If appropriate, a plurality of reactors can also be combined in a multistage apparatus. Such reactors are, for example, loop reactors with built-in sieve trays, cascaded vessels, tube reactors with intermediate feed points or stirred columns.

In a further process variant, the reaction can be carried out in a reactive distillation column. Such columns have a long residence time of the reaction solution in the respective stage. Thus, for example, columns which have a high liquid hold-up, e.g, highly banked-up trays of a tray column, can advantageously be used.

Preference is given to using stirred tank reactors. The stirred tank reactors are usually made of metallic materials, with stainless steel being preferred. The reaction mixture is preferably intensively mixed by means of a stirrer or a circulation pump.

Even though the process of the invention can be carried out using only one stirred tank, when the process is carried out continuously it is advantageous to connect a plurality of reactors to one another in the form of a cascade in order to obtain a substantially complete reaction. The reaction mixture passes through the individual reactors in succession, with the discharge from the first reactor being fed to the second reactor, the discharge from the second reactor being fed to the third reactor, etc. The cascade can comprise, for example, from 2 to 10 reactors, with from 3 to 6 reactors being preferred. Carboxylic acid and/or carboxylic anhydride and alcohol are introduced continuously into the first reactor.

During the reaction, an alcohol/water mixture is distilled off as azeotrope from the reaction mixture. In addition, further alcohol is fed into the reactor or the individual reactors of the reaction system during the reaction. The addition of additional alcohol can be dispensed with in the reactors into which alcohol vapor is introduced; if appropriate, additional liquid alcohol can be added. Further liquid alcohol is preferably fed into the reactors into which no alcohol vapor is introduced.

If the reaction system comprises a cascade of a plurality of reactors, alcohol vapor is introduced into the reaction mixture in at least one reactor, preferably at least into the reaction mixture in the last reactor. In the reactors of a cascade, the degree of conversion increases monotonically from the first to last reactor. The stripping by means of alcohol vapor according to the invention aids the removal of the remaining small amounts of water of reaction, especially in the latter reactors of a cascade.

If more than one reactor is treated with alcohol vapor, the alcohol vapor can be fed in parallel to the individual reactors or the alcohol vapor passes through a plurality of reactors in succession. Combinations in which fresh alcohol vapor is bubbled through two or more reactors and the vapor from at least one of the reactors is passed through at least one further reactor are also conceivable. In the case of parallel supply with alcohol vapor, each reactor through which alcohol vapor is to be bubbled is connected via an alcohol vapor line to the alcohol vaporizer.

If the alcohol vapor passes through a plurality of reactors in succession, the vapor from a reactor into which alcohol vapor is introduced is collected and the vapor is introduced in vapor form into the reaction mixture in at least one of the preceding reactors. The fresh alcohol vapor has to be introduced under sufficient pressure to overcome the cumulated hydrostatic pressure of the reaction mixture in the reactors through which it is to pass in succession. In this case, the pressure gradient between the reactors is sufficient for the collected vapor to be able to bubble through the reaction mixture in the preceding reactor. Otherwise, the collective vapor can be compressed before it is introduced into the preceding reactor. For example, in the case of a cascade of six reactors, it is possible to introduce fresh alcohol vapor into the reaction mixture in the last reactor, collect the vapor from the last reactor and introduce it in vapor form into the reaction mixture in the fifth reactor, collect the vapor from the fifth reactor and introduce it in vapor form into the reaction mixture in the fourth reactor.

In general, the vapor from at least one reactor is at least partly condensed, the condensate is separated into a liquid phase and an alcohol phase and the alcohol phase is recirculated at least partly into the reaction system. "Recirculation into the reaction system" means that the alcohol phase is introduced into at least one reactor which may be chosen freely of the reaction system.

The condensation or partial condensation of the vapor can be effected using all suitable condensers. These can be cooled by means of any cooling media. Condensers having air cooling and/or water cooling are preferred, and air cooling is particularly preferred.

The condensate obtained is subjected to a phase separation into an aqueous phase and an organic phase. For this purpose, the condensate is usually introduced into a phase separator (decanter) where it separates by mechanical settling into two phases which can be taken off separately. The aqueous phase is separated off and can, if appropriate after work-up, be discarded or used as stripping water in the after-treatment of the ester.

The vapor from the individual reactors of a cascade can be combined and condensed jointly. If appropriate, a plurality of reactors of a cascade can be combined to form one subunit, with the subunits then each being coupled to a condenser. It is also possible to couple each reactor of the cascade with a condenser.

The alcohol phase to be recirculated can be passed into any reactor of a cascade or distributed over a plurality of reactors of the cascade. However, the alcohol phase to be recirculated is preferably not introduced into the last reactor of the cascade. The alcohol phase to be recirculated is preferably introduced exclusively or predominantly into the first reactor of the cascade.

There are various possibilities for the recirculation of the alcohol phase into the reaction system. One possibility is to pump the organic phase, if appropriate after heating, into the liquid reaction mixture.

However, to thermally optimize the process, the alcohol phase is preferably recirculated into the reaction system via a column (known as recycle alcohol column) in which the alcohol phase to be recirculated is conveyed in countercurrent to at least part of the vapor. The alcohol phase is advantageously introduced into the recycle alcohol column at the top or in the upper region. The descending condensate of the recycle alcohol column goes back into the reaction system, when a reactor cascade is used preferably into the first reactor. The recirculation of the alcohol phase via the recycle alcohol column has the advantage that the recirculated alcohol phase is preheated and freed of traces of water which have remained in the organic phase after the phase separation or are, in accordance with their thermodynamic solubility, dissolved in the organic phase. The recycle alcohol column can be, for example, a tray column, a column having ordered packing or a column having random packing elements. A small number of theoretical plates is generally sufficient. A column having, for example, from 2 to 10 theoretical plates is suitable.

When a reactor cascade is used, the vapor preferably leaves at least the first reactor via the recycle alcohol column. One or more or all further reactors can likewise have a vapor offtake to the recycle alcohol column.

The process of the invention can in principle be applied to all esterifications in which the water of reaction is separated off by distillation as azeotrope with an alcohol.

In the process of the invention, carboxylic acids or carboxylic anhydrides are used as acid component. In the case of polybasic carboxylic acids, it is also possible to use partial anhydrides. It is likewise possible to use mixtures of carboxylic acids and anhydrides.

These acids can be aliphatic, including carbocyclic, heterocyclic, saturated or unsaturated, or else aromatic, including heteroaromatic.

Suitable carboxylic acids include aliphatic monocarboxylic acids having at least 5 carbon atoms, in particular from 5 to 20 carbon atoms, e.g. n-pentanoic acid, 2-methylbutyric acid, 3-methylbutyric acid, 2-methylpentanoic acid, 2-ethylbutyric acid, n-heptanoic acid, 2-methylhexanoic acid, isoheptanoic acids, cyclohexanecarboxylic acid, n-octanoic acid, 2-ethylhexanoic acid, isooctanoic acids, n-nonanoic acid, 2-methyloctanoic acid, isononanoic acid, n-decanoic acid, isodecanoic acids, 2-methylundecanoic acid, isoundecanoic acid, tricyclodecanecarboxylic acid and isotridecanecarboxylic acid.

Further suitable carboxylic acid components are aliphatic $C_4$-$C_{10}$-dicarboxylic acids or anhydrides thereof, e.g. maleic acid, fumaric acid, maleic anhydride, succinic acid, succinic anhydride, adipic acid, subacic acid, trimethyladipic acid, azelaic acid, decanedioic acid, dodecanedioic acid, brassylic acid. Examples of carbocyclic compounds are: 1,2-cyclohexanedicarboxylic acid (hexahydrophthalic acid), 1,2-cyclohexanedicarboxylic anhydride (hexahydrophthalic anhydride), cyclohexane-1,4-dicarboxylic acid, cyclohex-4-ene-1,2-dicarboxylic acid, cyclohexene-1,2-dicarboxylic anhydride, 4-methylcyclohexane-1,2-dicarboxylic acid, 4-methylcyclohexane-1,2-dicarboxylic anhydride, 4-methylcyclohex-4-ene-1,2-dicarboxylic acid, 4-methylcyclohex-4-ene-1,2-dicarboxylic anhydride.

Examples of suitable aromatic dicarboxylic acids or anhydrides thereof are: phthalic acid, phthalic anhydride, isophthalic acid, terephthalic acid or naphthalenedicarboxylic acids and anhydrides thereof.

Examples of suitable aromatic tricarboxylic acids (or anhydrides) are trimellitic acid, trimellitic anhydride or trimesic acid; an example of a suitable aromatic tetracarboxylic acid or anhydride thereof is pyromellitic acid and pyromellitic anhydride.

Particular preference is given to using phthalic anhydride as carboxylic acid component in the process of the invention.

Preference is given to using branched or linear aliphatic alcohols having from 4 to 13 carbon atoms in the process of the invention. The alcohols are monohydric and can be secondary or primary.

The alcohols used can originate from various sources. Suitable starting materials are, for example, fatty alcohols, alcohols from the Alfol process or alcohols or alcohol mixtures obtained by hydrogenation of saturated or unsaturated aldehydes, in particular ones whose synthesis includes a hydroformylation step.

Alcohols which are used in the process of the invention, are, for example, n-butanol, isobutanol, n-octan-1-ol, n-octan-2-ol, 2-ethylhexanol, nonanols, decyl alcohols or tridecanols prepared by hydroformylation or aldol condensation and subsequent hydrogenation. The alcohols can be used as pure compounds, as a mixture of isomeric compounds or as a mixture of compounds having different numbers of carbon atoms. A preferred example of such an alcohol mixture is a $C_9$/$C_{11}$-alcohol mixture.

Preferred feed alcohols are mixtures of isomeric octanols, nonanols or tridecanols, with the latter being able to be obtained from the corresponding butene oligomers, in particular oligomers of linear butenes, by hydroformylation and subsequent hydrogenation. The preparation of the butene oligomers can in principle be carried out by three methods. Acid-catalyzed oligomerization, in which, for example, zeolites or phosphoric acid on supports are used industrially, gives the most branched oligomers. For example, the use of linear butenes gives a $C_8$ fraction comprising essentially dimethylhexenes (WO 92/13818). A process which is likewise practiced worldwide is oligomerization using soluble Ni complexes, known as the DIMERSOL process (B. Cornils, W. A. Herrmann, Applied Homogenous Catalysis with Organometallic Compounds, pages 261-263, Verlag Chemie 1996). In addition, oligomerization is carried out over fixed-bed nickel catalysts, for example the OCTOL process (Hydrocarbon Process., Int. Ed. (1986) 65 (2. Sect. 1), pages 31-33) or the process as described in WO 95/14647 or WO 01/36356.

Very particularly preferred starting materials for the esterification according to the invention are mixtures of isomeric nonanols or mixtures of isomeric tridecanols prepared by oligomerization of linear butenes to $C_8$-olefins and $C_{12}$-olefins by the octol process or as described in WO 95/14647, with subsequent hydroformylation and hydrogenation.

Further suitable alkyls are alkylene glycol monoethers, in particular ethylene glycol monoethers such as ethylene glycol monomethyl ether, ethylene glycol monoethyl ether and ethylene glycol monobutyl ether; and polyalkylene glycol monoethers, in particular polyethylene glycol monoethers such as polyethylene glycol monomethyl ether.

Particularly preferred alcohols are 2-ethylhexanol, 2-propylheptanol, isononanol isomer mixtures, decanol isomer mixtures and $C_9/C_{11}$-alcohol mixtures.

The esterification according to the invention can be autocatalyzed or can be carried out in the presence of an esterification catalyst. The esterification catalyst is appropriately selected from among Lewis acids such as alkoxides, carboxylates and chelate compounds of titanium, zirconium, tin, aluminum and zinc; boron trifluoride, boron trifluoride etherates; mineral acids such as sulfuric acid, phosphoric acid; and sulfonic acids such as methanesulfonic acid and toluenesulfonic acid, and ionic liquids.

The esterification catalyst is appropriately selected from among alkoxides, carboxylates and chelate compounds of titanium, zirconium, tin, aluminum and zinc. Suitable catalysts are tetraalkyl titanates such as tetramethyl titanate, tetraethyl titanate, tetra-n-propyl titanate, tetraisopropyl titanate, tetra-n-butyl titanate, tetraisobutyl titanate, tetra-sec-butyl titanate, tetraoctyl titanate, tetra(2-ethylhexyl) titanate; dialkyl titanates ($(RO)_2TiO_2$, where R is, for example, isopropyl, n-butyl, isobutyl), e.g. isopropyl n-butyl titanate; titanium acetylacetonate chelates such as diisopropoxy bis(acetylacetonate)titanate, diisopropoxy bis(ethylacetylacetonate)titanate, di-n-butyl bis(acetylacetonate)titanate, di-n-butyl bis(ethylacetoacetato) titanate, triisopropoxy bis(acetylacetonate)titanate; zirconium tetraalkoxides such as zirconium tetraethoxide, zirconium tetrabutoxide, zirconium tetrabutyrate, zirconium tetrapropoxide, zirconium carboxylates such as zirconium diacetate; zirconium acetylacetonate chelates such as zirconium tetra(acetylacetonate), tributoxyzirconium acetylacetonate, dibutoxyzirconium bisacetylacetonate; aluminum trisalkoxides such as aluminum triisopropoxide, aluminum trisbutoxid; aluminum acetylacetonate chelates such as aluminum tris(acetylacetonate) and aluminum tris(ethylacetylacetonate). In particular, isopropyl n-butyl titanate, tetra(isopropyl) orthotitanate or tetra(butyl) orthotitanate are used.

Suitable ionic liquids are, for example, 1-(4-sulfobutyl)-3-methylimidazolium triflate and 1-ethyl-3-methylimidazolium hydrogensulfate.

Other suitable esterification catalysts are selected from among acidic ion exchangers, zeolites, oxides and/or hydroxides of magnesium, aluminum, zinc, titanium, silicon, tin, lead, antimony, bismuth, molybdenum and manganese.

The catalyst concentration depends on the type of the catalyst. In the case of the titanium compounds which are preferably used, this is from 0.005 to 1.0% by weight based on the reaction mixture, in particular from 0.01 to 0.3% by weight.

When the process is carried out batchwise, the starting materials and the catalyst can be introduced into the reactor either simultaneously or in succession. The catalyst can be introduced in pure form or as a solution, preferably as a solution in one of the starting materials, at the beginning or only after the reaction temperature has been reached. Carboxylic anhydrides frequently react autocatalytically, i.e. in the absence of catalysts, with alcohols to form the corresponding ester carboxylic acids (half esters), for example phthalic anhydride to form the monoester of phthalic acid. A catalyst is therefore frequently necessary only after the first reaction step.

In the case of a continuous process, streams of the starting materials and of the catalyst are fed into the reactor or, when a reactor cascade is used, into the first reactor of the cascade. The residence time in the reactor or the individual reactors is determined by the volume of the reactors and the flow of the starting materials.

The alcohol to be reacted, which serves as entrainer, can be used in a stoichiometric excess, preferably from 30 to 200%, particularly preferably from 50 to 100%, of the stoichiometrically required amount.

The reaction temperatures are in the range from 160° C. and 270° C. The optimal temperatures depend on the starting materials, the progress of the reaction and the catalyst concentration. They can easily be determined experimentally for each individual case. Higher temperatures increase the reaction rates and promote secondary reactions such as elimination of water from alcohols to form olefins or the formation of colored by-products. To remove the water of reaction, it is necessary for the alcohol to be able to be distilled off from the reaction mixture. The desired temperature or the desired temperature range can be set via the pressure in the reactor. In the case of low-boiling alcohols, the reaction can therefore be carried out under superatmospheric pressure and in the case of relatively high-boiling alcohols under reduced pressure. For example, the reaction of phthalic anhydride with a mixture of isomeric nonanols in the temperature range from 170° C. to 250° C. is carried out in the pressure range from 200 mbar to 3 bar.

All reactors of a cascade can be operated at the same temperature. However, preference is generally given to steadily increasing the temperature from the first to last reactor of a cascade, with a reactor being operated at the same temperature or a higher temperature than the reactor located upstream in the flow direction of the reaction mixture. All reactors can advantageously be operated at essentially the same pressure.

After the reaction is complete, the reaction mixture, which comprises essentially the desired ester and excess alcohol, further comprises not only the catalyst and/or its reaction products but also small amounts of ester carboxylic acid(s) and/or unreacted carboxylic acid.

To work up these crude ester mixtures, the excess alcohol is removed, the acidic compounds are neutralized, the catalyst is destroyed and the solid by-products formed are separated off. Here, the major part of the unreacted alcohol is distilled off at atmospheric pressure or under reduced pressure. The last traces of the alcohol can be removed, for example, by steam distillation, in particular in the temperature range from 120 to 225° C. under reduced pressure. The removal of the alcohol can be carried out as first or last work-up step.

The neutralization of the acidic substances such as carboxylic acids, ester carboxylic acids or if appropriate the acidic catalysts is effected by addition of bases, e.g. alkali metal and/or alkaline earth metal carbonates, hydrogencarbonates or hydroxides. The neutralizing agent can be used in solid form or preferably as a solution, in particular as an aqueous solution. Here, sodium hydroxide solution having a concentration of from 1 to 30% by weight, preferably from 20 to 30% by weight, is frequently used. The neutralizing agent is used in an amount corresponding to from one to four times, in particular from one to two times, the stoichiometrically required amount determined by titration.

The esters of polybasic carboxylic acids, for example phthalic acid, adipic acid, sebacic acid, maleic acid, and alcohols which have been prepared in this way are used further in surface coating resins, as constituents of paints and in particular as plasticizers for plastics. Suitable plasticizers for PVC are dioctyl phthalate, diisononyl phthalate, diisodecyl phthalate and dipropylheptyl phthalate.

The invention is illustrated by the accompanying drawing and the following examples.

FIG. 1 shows a plant suitable for carrying out the process of the invention. The plant comprises a cascade of six stirred vessels 1, 2, 3, 4, 5 and 6, with the outflow from the first vessel being fed to the second vessel, the outflow from the second vessel being fed to the third vessel, etc. Alcohol is fed via an alcohol manifold (not shown) and feed lines into the stirred vessels 1, 2, 3, 4 and 5. An acid component, for example phthalic anhydride (PAn), is fed via line 7 into the first vessel 1. Esterification catalyst is introduced into the first vessel 1 via line 8.

The vapors rising out from the first vessel 1 are taken off via line 10 and go into the recycle alcohol column 9; the runback from the recycle alcohol column 9 goes via line 11 to the first vessel 1. The vapor offtakes 12, 13, 14 from the second, third and fourth vessels 2, 3, 4 likewise lead to the recycle alcohol column 9.

The combined vapors are fed to a condenser 15, e.g. an air-cooled condenser. The mixed-phase stream leaving the condenser 15 is separated in the phase separator 16. The lower, aqueous phase is taken off via a line (not shown) and discarded. The upper, organic phase is fed via line 17 into the recycle alcohol collection vessel 18. Part of the organic phase can be discharged from the system or treated, e.g. purified, to avoid accumulation of by-products and fed to the recycle alcohol collection vessel 18.

Alcohol from the recycle alcohol collection vessel 18 is fed via the pump 19 and line 20 into the recycle alcohol column 9 at the top or in the upper region and there is conveyed in countercurrent to the ascending vapor and goes via line 11 into the first vessel 1.

Alcohol is fed via line 21 to the vaporizer 22, e.g. a shell-and-tube vaporizer, and vaporized. The vaporizer 22 is heated by means of hot steam which is supplied via line 23. The hot steam condensate is discharged via line 24. The alcohol vapor generated is fed via line 25 and the ring of nozzles 26 below the surface of the liquid into the reaction mixture in vessel 6. The alcohol vapor bubbles through the reaction mixture; the stripping effect aids the removal of the water of reaction as alcohol-water azeotrope. The vapors in the gas space of the vessel 6 are collected via line 27 and introduced via the ring of nozzles 28 below the surface of the liquid into the reaction mixture in vessel 5. The pressure difference between the vessel 6 and the vessel 5 is sufficient for the vapors from the vessel 6 to be able to overcome the hydrostatic pressure of the reaction mixture above the ring of nozzles 28 in the vessel 5 without additional compression. The vapors in the gas space of the vessel 5 are collected via line 29 and introduced via the ring of nozzles 30 below the surface of the liquid into the reaction mixture in the vessel 4.

EXAMPLES

Comparative Example 1

Preparation of Diisononyl Phthalate

The continuous preparation of diisononyl phthalate (DINP) was carried out using a cascade of six stirred vessels. Isononanol was fed into each reaction vessel, a total of 731 g/h of isononanol. 0.3 g/h of propyl titanate were fed into the first reaction vessel. In addition, 358 g/h of phthalic anhydride (PAn) were introduced into the first reaction vessel. In addition, by means of a recycle alcohol column on the first stirred vessel, about 665 g/h of isononanol recycle stream were fed as runback to the recycle alcohol column.

The vapors from the first stirred vessel were taken off via the recycle alcohol column whose runback was fed back into the first stirred vessel. The offtake of vapor from the second to third stirred vessel likewise occurred via the recycle alcohol column; the vapors from the fourth to sixth stirred vessel were taken off directly.

The vapors from the esterification were condensed in an air condenser and the condensate was cooled to a temperature of 70° C. The organic and aqueous phases were separated at atmospheric pressure in a phase separator. The water was discharged from the system; part of the organic phase was fed to an alcohol collection vessel.

The crude ester mixture flowing out from the last stirred vessel was worked up by removing the excess alcohol, neutralizing the acidic compounds, destroying the catalyst and separating off the solid by-products formed. This gave 1000 g/h of DINP having an acid number of 0.5 mg KOH/g.

Example 1

The continuous preparation of DINP was carried out in a manner analogous to comparative example 1, but isononanol vapor produced by vaporization of 105 g/h of isononanol in a vaporizer was introduced into the sixth stirred vessel 30 cm below the level of the liquid reaction mixture and replaced the addition of liquid isononanol to this vessel. The vapors from the sixth vessel were fed into the fifth vessel below the surface of the liquid reaction mixture, and the vapors from the fifth vessel were fed into the fourth vessel below the surface of the liquid reaction mixture.

The acid number of the DINP formed was more than 80% lower than in comparative example 1; the space-time yield increased by more than 30%.

The invention claimed is:

1. A process for preparing carboxylic esters by reaction of a reaction mixture comprising a carboxylic acid and/or a carboxylic anhydride and an alcohol in the presence of an esterification catalyst selected from group consisting of alkoxides, carboxylates and chelate compounds of titanium, zirconium, tin, aluminum and zinc, in a reaction system comprising one or more stirred tank reactors, with water of reaction being distilled off as alcohol-water azeotrope with the vapor, where the vapor from at least one reactor is at least partly condensed, the condensate is separated into an aqueous phase and an alcohol phase and the alcohol phase is at least partly recirculated to the reaction system, wherein the reaction mixture is treated with superheated alcohol vapor, wherein the alcohol vapor is introduced below the surface of the liquid reaction mixture and the alcohol vapor bubbles through the reaction mixture, and wherein the temperature of the superheated alcohol vapor is at least 20° C. higher than the dew point.

2. The process according to claim 1, wherein the reaction mixture is mixed in order to effect exchange of reaction mixture in the reactor region below the introduction of alcohol vapor with reaction mixture in the reactor region above the introduction of alcohol vapor.

3. The process according to claim 1, wherein the reaction system comprises a cascade of a plurality of reactors and alcohol vapor is introduced into the reaction mixture in more than one reactor.

4. The process according to claim 1, wherein the reaction system comprises a cascade of a plurality of reactors and alcohol vapor is introduced at least into the reaction mixture in the last reactor.

5. The process according to claim 3, wherein the vapor from the last reactor is collected and introduced in vapor form into the reaction mixture in at least one of the preceding reactors.

6. The process according to claim 1, wherein the alcohol phase is recirculated to the reaction system via a column in which the recirculated alcohol phase is conveyed in countercurrent to at least part of the vapor.

7. The process according to claim 6, wherein the reaction system comprises a cascade of a plurality of reactors and the alcohol phase is recirculated exclusively or predominantly into the first reactor of the cascade.

8. The process according to claim 1, wherein the carboxylic acid is selected from the group comprising of aliphatic monocarboxylic acids having at least 5 carbon atoms, aliphatic $C_4$-$C_{10}$-dicarboxylic acids, aromatic monocarboxylic acids, aromatic dicarboxylic acids, aromatic tricarboxylic acids, aromatic tetracarboxylic acids and anhydrides thereof.

9. The process according to claim 1, wherein the alcohol is selected from the group comprising of $C_4$-$C_{13}$-alcohols, alkylene glycol monoethers and polyalkylene glycol monoethers and mixtures thereof.

\* \* \* \* \*